(12) United States Patent
Agrawal et al.

(10) Patent No.: US 11,291,821 B2
(45) Date of Patent: Apr. 5, 2022

(54) HEMOSTASIS VALVES AND METHODS FOR MAKING AND USING HEMOSTASIS VALVES

(71) Applicant: BOSTON SCIENTIFIC LIMITED, Hamilton (BM)

(72) Inventors: Sumit Agrawal, Haryana (IN); Henry J. Pepin, Loretto, MN (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 740 days.

(21) Appl. No.: 15/905,064

(22) Filed: Feb. 26, 2018

(65) Prior Publication Data
US 2018/0256873 A1    Sep. 13, 2018

Related U.S. Application Data

(60) Provisional application No. 62/470,692, filed on Mar. 13, 2017.

(51) Int. Cl.
*A61M 39/06* (2006.01)
*A61M 5/00* (2006.01)

(52) U.S. Cl.
CPC ........ *A61M 39/0613* (2013.01); *A61M 39/06* (2013.01); *A61M 39/0606* (2013.01); *A61M 5/007* (2013.01); *A61M 2039/064* (2013.01); *A61M 2039/0673* (2013.01)

(58) Field of Classification Search
CPC .... A61M 2039/064; A61M 2039/0673; A61M 39/06; A61M 39/0606; A61M 39/0613; A61M 5/007
See application file for complete search history.

(56) References Cited

U.S. PATENT DOCUMENTS

| | | | |
|---|---|---|---|
| 2,833,568 | A | 5/1958 | Corsette |
| 3,095,175 | A | 6/1963 | Taisho |
| 3,685,786 | A | 8/1972 | Woodson |
| 4,612,010 | A | 9/1986 | Hamacher et al. |
| 4,723,550 | A | 2/1988 | Bales et al. |

(Continued)

FOREIGN PATENT DOCUMENTS

| | | |
|---|---|---|
| CN | 1946451 A | 4/2007 |
| CN | 101918064 A | 12/2010 |

(Continued)

OTHER PUBLICATIONS

International Search Report and Written Opinion dated Jun. 20, 2018 for International Application No. PCT/US2018/019712.

(Continued)

*Primary Examiner* — Brandy S Lee
(74) *Attorney, Agent, or Firm* — Seager, Tufte & Wickhem LLP.

(57) ABSTRACT

Hemostasis valves and methods for making and using hemostasis valves are disclosed. An example hemostasis valve may include a main body having a proximal end region. A cartridge may be at least partially disposed within the proximal end region. The cartridge including a seal member. The cartridge may have a proximal member, a distal member, and may define a seal holding region. The seal member may have an axial thickness of about 0.04 to about 0.2 inches. The seal member may be secured within the seal holding region by a mechanical bond.

20 Claims, 10 Drawing Sheets

(56) References Cited

U.S. PATENT DOCUMENTS

| | | |
|---|---|---|
| 4,857,062 A | 8/1989 | Russell |
| 4,875,062 A | 10/1989 | Rakov |
| 4,895,346 A | 1/1990 | Steigerwald |
| 4,925,450 A | 5/1990 | Imonti et al. |
| 4,932,114 A | 6/1990 | Morse et al. |
| 4,932,633 A | 6/1990 | Johnson et al. |
| 4,978,341 A | 12/1990 | Niederhauser |
| 5,009,391 A | 4/1991 | Steigerwald |
| 5,030,206 A | 7/1991 | Lander |
| 5,049,071 A | 9/1991 | Davis et al. |
| 5,059,186 A | 10/1991 | Yamamoto et al. |
| 5,060,987 A | 10/1991 | Miller |
| 5,078,433 A | 1/1992 | Morse et al. |
| 5,078,688 A | 1/1992 | Lobodzinksi et al. |
| 5,098,393 A | 3/1992 | Amplatz et al. |
| 5,106,054 A | 4/1992 | Mollenauer et al. |
| 5,135,492 A | 8/1992 | Melker et al. |
| 5,154,701 A | 10/1992 | Cheer et al. |
| 5,158,553 A | 10/1992 | Berry et al. |
| 5,161,773 A | 11/1992 | Tower |
| 5,167,636 A | 12/1992 | Clement |
| 5,195,980 A | 3/1993 | Catlin |
| 5,197,463 A | 3/1993 | Jeshuran |
| 5,203,774 A | 4/1993 | Gilson et al. |
| 5,205,831 A | 4/1993 | Ryan et al. |
| 5,224,929 A | 7/1993 | Remiszewski |
| 5,241,990 A | 9/1993 | Cook |
| 5,269,764 A | 12/1993 | Vetter et al. |
| 5,269,771 A | 12/1993 | Thomas et al. |
| 5,273,546 A | 12/1993 | Mclaughlin et al. |
| 5,282,790 A | 2/1994 | Clement |
| 5,299,843 A | 4/1994 | Weigl et al. |
| 5,324,271 A | 6/1994 | Abiuso et al. |
| 5,338,313 A | 8/1994 | Mollenauer et al. |
| 5,350,205 A | 9/1994 | Aldridge et al. |
| 5,350,364 A | 9/1994 | Stephens et al. |
| 5,352,215 A | 10/1994 | Thome et al. |
| 5,356,394 A | 10/1994 | Farley et al. |
| 5,364,371 A | 11/1994 | Kamen |
| 5,376,077 A | 12/1994 | Gomringer |
| 5,382,230 A | 1/1995 | Bonn |
| 5,383,860 A | 1/1995 | Lau |
| 5,389,090 A | 2/1995 | Fischell et al. |
| 5,395,349 A | 3/1995 | Quiachon et al. |
| 5,460,615 A | 10/1995 | Storz |
| 5,514,109 A | 5/1996 | Mollenauer et al. |
| 5,542,933 A | 8/1996 | Marks |
| 5,562,611 A | 10/1996 | Transue |
| 5,569,208 A | 10/1996 | Woelpper et al. |
| 5,575,767 A | 11/1996 | Stevens |
| 5,584,314 A | 12/1996 | Bron |
| 5,591,137 A | 1/1997 | Stevens |
| 5,599,327 A | 2/1997 | Sugahara et al. |
| 5,651,170 A | 7/1997 | Stevens |
| 5,693,025 A | 12/1997 | Stevens |
| 5,911,710 A | 6/1999 | Barry et al. |
| 5,921,968 A | 7/1999 | Lampropoulos et al. |
| 5,935,112 A | 8/1999 | Stevens et al. |
| 5,935,122 A | 8/1999 | Fourkas et al. |
| 5,992,899 A | 11/1999 | Strowe |
| 6,287,280 B1 | 9/2001 | Lampropoulos et al. |
| 6,331,176 B1 | 12/2001 | Becker et al. |
| 6,402,723 B1 | 6/2002 | Lampropoulos et al. |
| 6,458,103 B1 | 10/2002 | Albert et al. |
| 6,551,283 B1 * | 4/2003 | Guo ............... A61M 39/06 251/149.1 |
| 6,572,590 B1 | 6/2003 | Stevens et al. |
| 6,695,818 B2 | 2/2004 | Wollschlger |
| 6,986,749 B2 | 1/2006 | Wollschlger |
| 7,172,580 B2 | 2/2007 | Hruska et al. |
| 7,938,809 B2 | 5/2011 | Lampropoulos et al. |
| 8,777,893 B2 | 7/2014 | Malewicz |
| 9,592,372 B2 | 3/2017 | Myers |
| 2001/0021825 A1 | 9/2001 | Becker et al. |
| 2004/0172008 A1 | 9/2004 | Layer |
| 2004/0210194 A1 | 10/2004 | Bonnette et al. |
| 2005/0033239 A1 | 2/2005 | Argentine |
| 2005/0171479 A1 | 8/2005 | Hruska et al. |
| 2007/0106262 A1 | 5/2007 | Becker et al. |
| 2007/0225648 A1 * | 9/2007 | Winsor ............ A61M 39/045 604/167.04 |
| 2008/0157017 A1 | 7/2008 | Macatangay et al. |
| 2008/0208175 A1 | 8/2008 | Beckman et al. |
| 2009/0259200 A1 * | 10/2009 | Lampropoulos .. A61M 39/0613 604/249 |
| 2013/0006176 A1 | 1/2013 | Miller |
| 2015/0038919 A1 * | 2/2015 | Bramwell ........ A61M 39/0606 604/246 |
| 2018/0126143 A1 | 5/2018 | Agrawal et al. |

FOREIGN PATENT DOCUMENTS

| | | |
|---|---|---|
| WO | 9945983 A1 | 9/1999 |
| WO | 2005107843 A1 | 11/2005 |
| WO | 2009002828 A2 | 12/2008 |

OTHER PUBLICATIONS

PCT Search Report and Written Opinion for PCT/US2009/039396 dated Apr. 3, 2009.

* cited by examiner

HEMOSTASIS VALVES AND METHODS FOR MAKING AND USING HEMOSTASIS VALVES

CROSS REFERENCE TO RELATED APPLICATIONS

This application claims the benefit of U.S. Provisional Patent Application Ser. No. 62/470,692 filed on Mar. 13, 2017, the disclosure of which is incorporated herein by reference.

TECHNICAL FIELD

The present disclosure pertains to medical devices, and methods for manufacturing medical devices. More particularly, the present disclosure pertains to hemostasis valves and methods for making and using hemostasis valves.

BACKGROUND

A wide variety of medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example hemostasis valve is disclosed. The hemostasis valve comprises: a main body having a proximal end region; a cartridge at least partially disposed within the proximal end region, the cartridge including a seal member; wherein the cartridge has a proximal member, a distal member, and defines a seal holding region; wherein the seal member has an axial thickness of 0.04-0.2 inches; and wherein the seal member is secured within the seal holding region by a mechanical bond.

Alternatively or additionally to any of the embodiments above, the mechanical bond includes a crimp.

Alternatively or additionally to any of the embodiments above, the seal member has an axial thickness of 0.075-0.095 inches.

Alternatively or additionally to any of the embodiments above, the seal member has a distal face with a distal slit, wherein the seal member has a proximal face with a proximal slit; and wherein the distal slit and the proximal slit are axially spaced 0.01-0.02 inches.

Alternatively or additionally to any of the embodiments above, the distal slit is arranged orthogonally with the proximal slit.

Alternatively or additionally to any of the embodiments above, further comprising a plunger coupled to the proximal end region of the main body.

Alternatively or additionally to any of the embodiments above, the seal member has a seal body and a peripheral region designed to engage the seal holding region of the cartridge.

Alternatively or additionally to any of the embodiments above, the peripheral leg region has a radial thickness of 0.001-0.02 inches.

Alternatively or additionally to any of the embodiments above, the central seal region has a width that is at least twice as large as a radial thickness of the peripheral leg region.

Alternatively or additionally to any of the embodiments above, the proximal end region of the main body includes one or more threads and further comprising a nut threadably engaged with the one or more threads.

A hemostasis valve is disclosed. The hemostasis valve comprises: a main body having a threaded proximal end region; a nut threadably engaged with the threaded proximal end region; a plunger coupled to the threaded proximal end region; a cartridge at least partially disposed within the threaded proximal end region, the cartridge including a seal member; wherein the seal member is secured within a seal holding region of the cartridge by a mechanical bond; and wherein the seal member has an axial thickness of 0.04-0.2 inches.

Alternatively or additionally to any of the embodiments above, the mechanical bond includes a crimp.

Alternatively or additionally to any of the embodiments above, the seal member has an axial thickness of 0.075-0.095 inches.

Alternatively or additionally to any of the embodiments above, the seal member has a distal face with a distal slit, wherein the seal member has a proximal face with a proximal slit; and wherein the distal slit and the proximal slit are axially spaced 0.01-0.02 inches.

Alternatively or additionally to any of the embodiments above, the distal slit is arranged orthogonally with the proximal slit.

Alternatively or additionally to any of the embodiments above, the seal member has a central seal region and a peripheral leg region designed to engage the seal holding region of the cartridge.

Alternatively or additionally to any of the embodiments above, the peripheral leg region has a radial thickness of 0.001-0.02 inches.

Alternatively or additionally to any of the embodiments above, the central seal region has a width that is at least twice as large as a radial thickness of the peripheral leg region.

A hemostasis valve is disclosed. The hemostasis valve comprises: a main body having a threaded proximal end region; a nut threadably engaged with the threaded proximal end region; a plunger coupled to the threaded proximal end region; a cartridge at least partially disposed within the threaded proximal end region, the cartridge including a seal member; wherein the seal member is secured within a seal holding region of the cartridge by a crimp bond; wherein the seal member has a central seal region and a peripheral leg region designed to engage the seal holding region of the cartridge; and wherein the central seal region has a width that is at least twice as large as a radial thickness of the peripheral leg region.

Alternatively or additionally to any of the embodiments above, the seal member has an axial thickness of 0.075-0.095 inches.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, for example intravascular procedures, utilize medical devices within body lumens. For example, some intravascular procedures include the placement of a guidewire, guide catheter, interventional device, or the like in a blood vessel. Because fluid under pressure (e.g., blood) is present within the blood vessel, fluid could travel along or through the medical device and escape or leak from the patient. In some instances, it may be desirable to dispose a hemostasis valve or hemostasis valve assembly at the proximal end of a medical device to reduce or otherwise limit the leaking of fluids/blood from the proximal end of the device.

Figure 1:
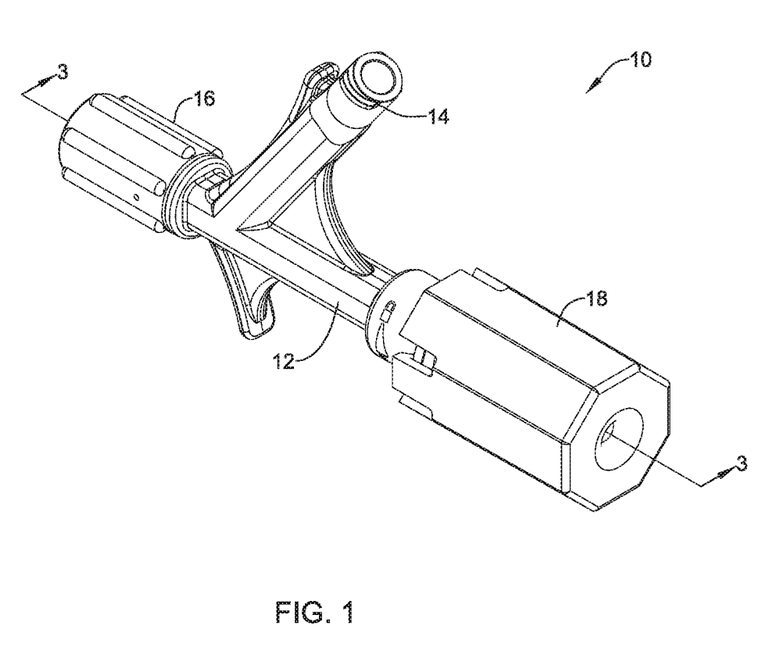
FIG. 1 is a perspective view of an example hemostasis valve.

An example hemostasis valve 10 is shown in FIG. 1. The hemostasis valve 10 may include a main body 12. The main body 12 may include a side port 14. The side port 14 may be connected to another device such as an infusion device, an inflation device, or the like. An adapter 16 may be coupled to the distal end of the main body 12. The adapter 16 may be used to couple the hemostasis valve 10 to a device such as a catheter. A plunger 18 may be coupled to the proximal end of the main body 12. The plunger 18 may be used to activate or otherwise close a seal (e.g., as discussed herein) within the hemostasis valve 10. These and other features of the hemostasis valve 10 are discussed herein.

Figure 2:
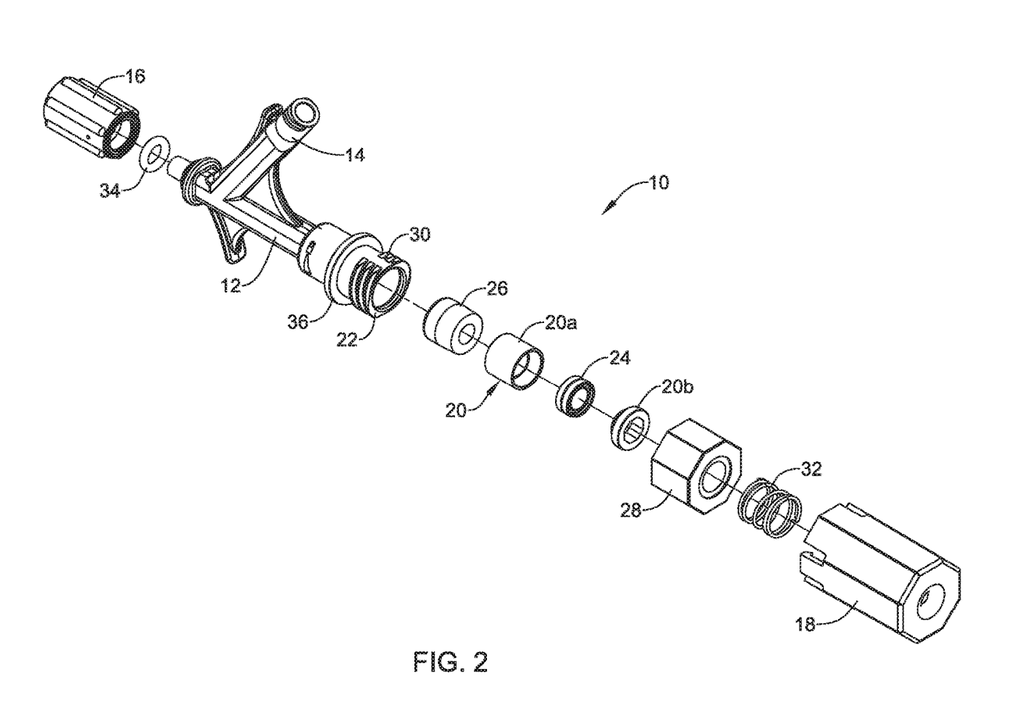
FIG. 2 is an exploded view of an example hemostasis valve.

FIG. 2 is an exploded view of the hemostasis valve 10. Here, the various components of the hemostasis valve 10 can be seen. For example, the hemostasis valve 10 may include a cartridge 20. The cartridge 20, which may include two pieces 20a, 20b that are coupled to one another (e.g., press fit, thermally bonded, adhesively bonded, etc.), may be arranged so that at least a portion thereof can be disposed within a proximal end region 22 of the main body 12. A first seal member 24 may be disposed within the cartridge 20. A second seal member 26 may be disposed within the proximal end region 22 of the main body 12. In at least some instances, the second seal member 26 may be disposed distally of the cartridge 20. The second seal member 26 may include a textured distal surface, grooves or wells formed therein, or the like. In addition or in the alternative, the second seal member 26 may include a proximal region with a reduced diameter. A nut 28 may be coupled to the proximal end region 22 of the main body 12, for example at one or more threads 30 formed along the proximal end region 22.

Other features of the hemostasis valve 10 that can be seen in FIG. 2 include a spring member 32 and an O-ring 34. The spring member 32 may be coupled to the plunger 18. In at least some instances, the spring member 32 may be designed to exert a proximally directed force on the plunger 18. The O-ring 34 may be positioned adjacent to the adapter 16. In addition, a ring member or "snap ring" 36 may be disposed along the proximal end region 22 of the main body 12.

Figure 3:
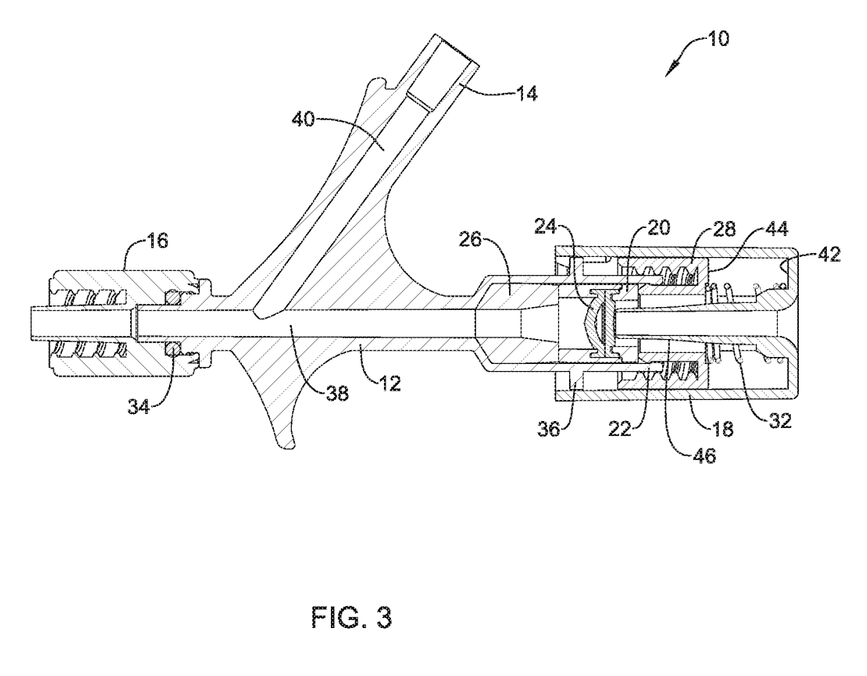
FIG. 3 is a cross-sectional view taken through line 3-3 in FIG. 1.

FIG. 3 is a cross-sectional view the hemostasis valve 10. Here some of the structural features of the hemostasis valve 10 can be seen. For example, the hemostasis valve 10 may include a central lumen 38. In general, the central lumen 38 is designed to be placed into fluid communication with one or more lumens of a device coupled to the adapter 16. A second or infusion lumen 40 may be defined adjacent to the side port 14. The second lumen 40 may be in fluid communication with the central lumen 38.

As indicated above, the hemostasis valve 10 is designed so that it may be coupled to another device. For example, the adapter 16, which may take the form of a Tuohy-Borst or other type of connector, may be engaged with the proximal end of the other device. When connected (and with the plunger 18 in the configuration shown in FIG. 3), the second seal member 26 may be in an open state or configuration. Conversely, the first seal member 24 may be in a closed or sealed configuration when the hemostasis valve 10 is connected to the other device (and with the plunger 18 in the configuration shown in FIG. 3).

Collectively, when the hemostasis valve 10 is connected to another device and in the configuration shown in FIG. 3, the hemostasis valve 10 is able to substantially hold a fluid-tight seal that substantially prevents the backflow and/or leakage of body fluids (e.g., blood). At some point during a medical intervention, it may be desirable to infuse additional fluids such as contrast media through the hemostasis valve 10. This may include attaching an infusion device to the side port 14. Because the first seal member 24 may be designed to substantially prevent the backflow and/or leakage of relatively-low pressure fluids, if the infusion device infuses fluids at a relatively high pressure, it is possible that the infusion fluid may be able to flow through the first seal member 24.

Figure 4:
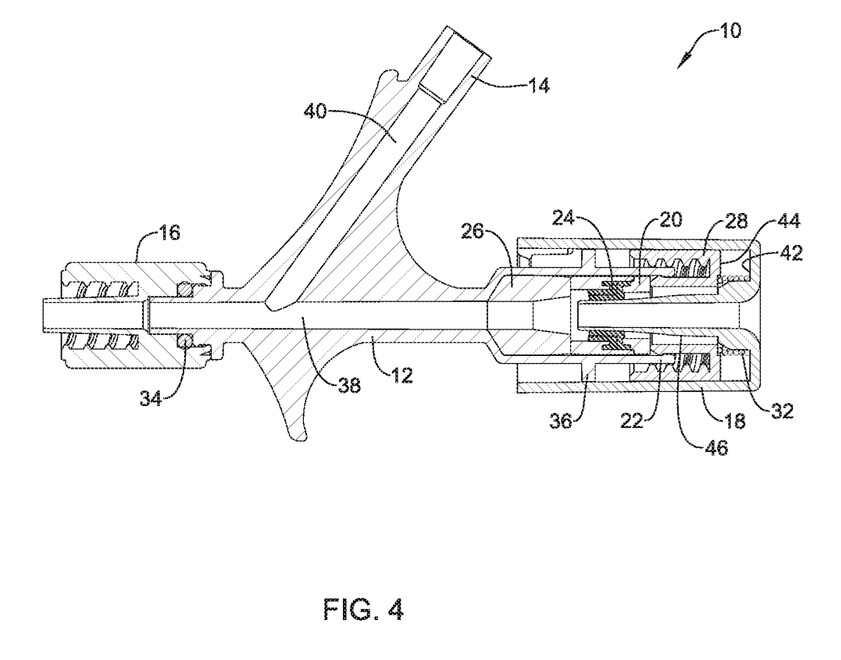
FIG. 4 is a cross-sectional view of an example hemostasis valve.
Figure 5A:
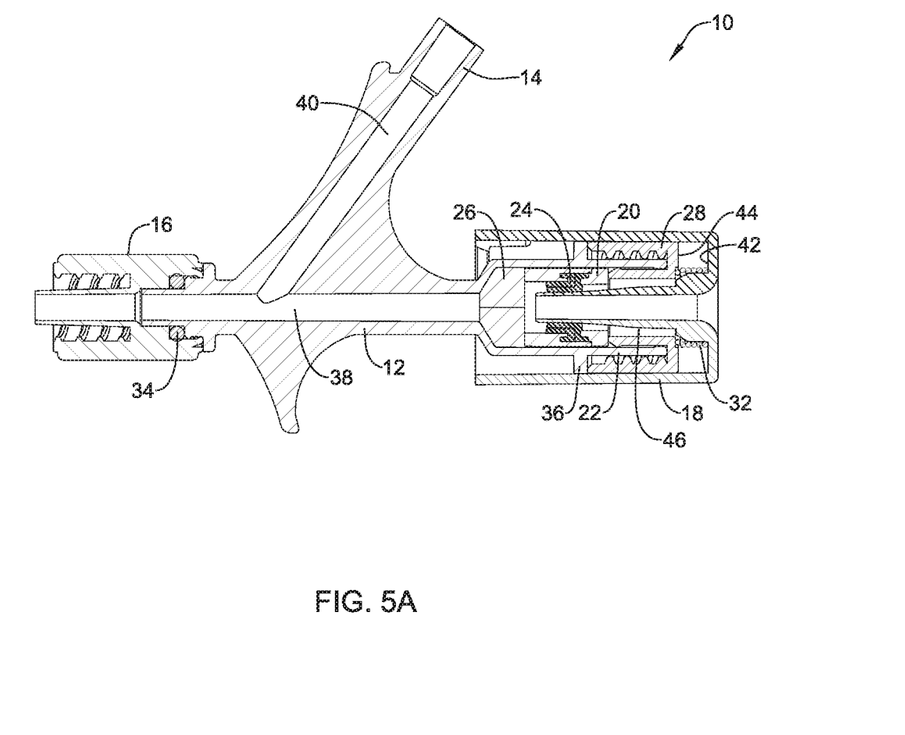
FIGS. 5A-5B is a cross-sectional view of an example hemostasis valve.
Figure 5B:
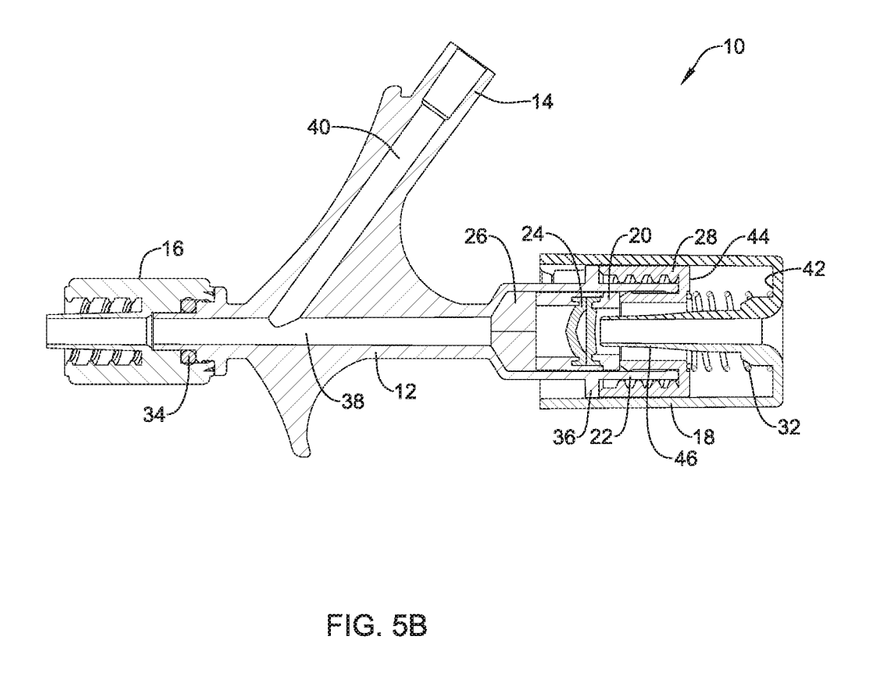

In order to prevent backflow of relatively high pressure fluids, the hemostasis valve 10 can be actuated to close or "seal" the second seal member 26. To do so, the plunger 18 may initially be urged distally until a distally-facing, proximal end surface or cap 42 of the plunger 18 is disposed adjacent to a proximal end region 44 of the nut 28 as shown in FIG. 4. When doing so, a tubular region 46 of the plunger 18 may extend through (and open) the first seal member 24. In addition, a portion of the plunger 18 may move distally beyond the ring member 36. With the cap 42 of the plunger 18 disposed adjacent to the nut 28, the plunger 18 can be rotated (e.g., in a clockwise direction) to close the second seal member 26 as shown in FIG. 5A. This rotation may cause the nut 28 to rotate and move distally. Because the distal end region of the nut 28 may be engaged with the cartridge 20, distal movement of the nut 28 urges the cartridge 20 distally within the proximal end region 22 of the main body 12 such that the cartridge 20 engages and deforms the second seal member 26, thereby shifting the second seal member 26 to the closed or sealed configuration. The plunger 18 may be released or otherwise allowed to move proximally, as shown in FIG. 5B, which may reclose the first seal member 24 (while the second seal member 26 remains closed).

As indicated above, the first seal member 24 may be described as a "low pressure" seal, designed to prevent the flow of fluids at a relatively low pressure. It may desirable to enhance the performance of the first seal member 24. Disclosed herein are hemostasis valves where the performance of the first seal member 24 is enhanced.

Figure 6:
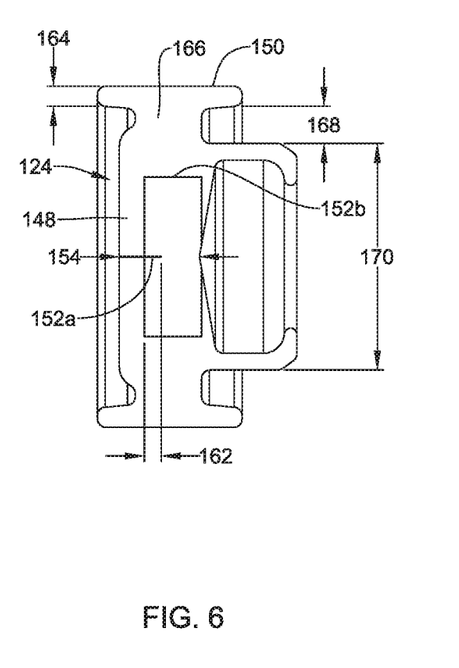
FIG. 6 is a side view of an example seal member.
Figure 7:
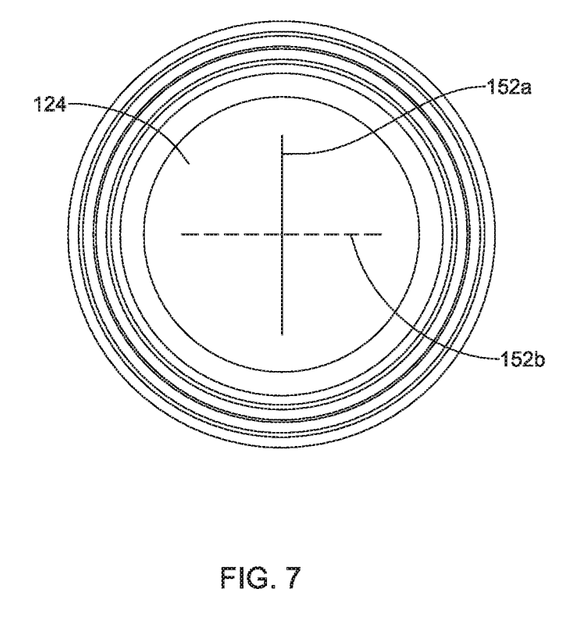
FIG. 7 is an end view of an example seal member.
Figure 8:
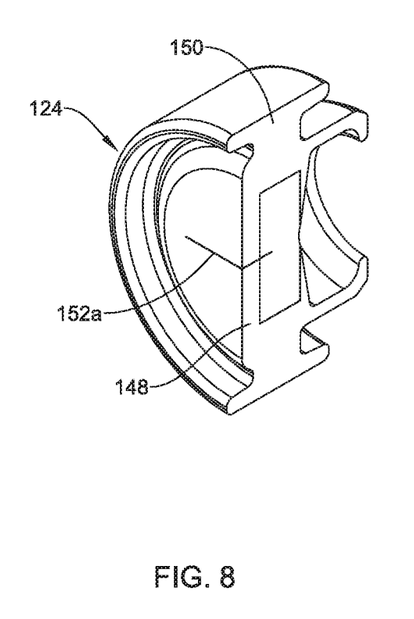
FIG. 8 is a perspective view of an example seal member.

FIGS. 6-8 illustrates an example seal member 124 that may be similar in form and function to other seal members disclosed herein (e.g., such as the first seal member 24) and may be used with the hemostasis valve 10 and/or other hemostasis valves. The seal member 124 may include a seal body 148 and a peripheral region 150. Because of its shape from a side view or in cross-section, the peripheral region 150 may be thought of as having "legs" or pairs of legs. A shoulder region 166 may be defined between the peripheral region 150 and the seal body 148.

The structural arrangement of the seal member 124 may be sized and shaped to provide a number of desired features. Some of the structural features may include a thickness or width 164 of the peripheral region 150, a thickness or width 168 of the shoulder region 166, a width 170 of the seal body 148, and a thickness 154 of the seal body 148. In some instances, the thickness 154 of the seal body 148 may be in the range of about 0.01-0.3 inches, or about 0.02-0.2 inches, or about 0.04-0.2 inches, or about 0.055-0.15 inches or so, or about 0.075-0.095 inches. For example, the thickness 154 of the seal body 148 may be about 0.045 inches, or about 0.055 inches, or about 0.075 inches, or about 0.095 inches.

In some instances, the width/thickness 164 of the peripheral region 150 may be relatively thin. For the purposes of this disclosure, "relatively thin" may be understood with respect to the dimensions of other structures of the seal member 124. For example, the width 164 of the peripheral region 150 may be smaller or thinner than the width 168 of the shoulder region 166 and/or thinner than the width 170 of the seal body 148. In some instances, the width 168 of the shoulder region 166 may be about 1.1-10 times the width 164 of the peripheral region 150, or about 1.5-5 times the width 164 of the peripheral region 150, or about 2-3 times the width 164 of the peripheral region 150. In some of these and in other instances, the width 170 of the seal body 148 may be about 1.1-15 times the width 164 of the peripheral region 150, or about 2-10 times the width 164 of the peripheral region 150, or about 3-5 times the width 164 of the peripheral region 150. In some of these and in other instances, the width 170 of the seal body 148 may be about 1.1-10 times the width 168 of the shoulder region 166, or about 1.5-5 times the width 168 of the shoulder region 166, or about 2-3 times the width 168 of the shoulder region 166.

Collectively, in at least some instances, the peripheral region 150 may be considered to be relatively thin and the width 170 of the seal body 148 may be considered to be relatively wide. While not wishing to be bound by theory, it is believed that utilizing the relatively thin peripheral region 150 and a relatively wide seal body 148 allows the seal body 148 to have a greater surface area for opening. This may reduce the deformation forces such that actuating the plunger (e.g., the plunger 18 as described above) may require less force (e.g., when compared with seal members with a smaller surface area and/or when compared with seal members where the ratio the size of the seal body to the size of the peripheral region is reduced). In addition, the structure/arrangement of the seal member 124 may allow the seal member 124 to accommodate larger devices therein/therethrough without becoming damaged.

The seal member 124 may be formed from a suitable material. For example, the seal member 124 may be formed from a silicone and/or silicone rubber material such as LSR6030, commercially available from Shenzhen SQUARE Silicone Co., Ltd. In some instances, the seal member 124 may be formed from an elastomeric material such as Q7-4720, Q7-4735, GUMSTOCK, or the like, which are commercially available from DOW CORNING.

The seal member 124 may have one or more slits such as a first slit 152a and a second slit 152b. The first slit 152a and the second slit 152b may come together at a slit interface 162. For the purposes of this disclosure, the slit interface 162 may be understood as the distance that the first slit 152a and the second slit 152b overlap. In some instances, the slit interface 162 may be about 0.005-0.05 inches, or about 0.01-0.05 inches, or about 0.01-0.02 inches, or about 0.015 inches.

The number and arrangement of the slits (e.g., the first slit 152a and the second slit 152b) may vary. In some instances, only a single slit may be utilized. The single slit may be disposed along the proximal face or the distal face of the seal body 148. In other instances, two or more slits may be arranged on the same side/face of the seal body 148. For example, two slits may be arranged orthogonally on the same side/face of the seal body 148. The opposing side/face may include zero, one, two, three, or more slit in a suitable arrangement. In some instances, one or more of the sides/faces of the seal body 148 may include slits that form a pattern such as a "star pattern". In at least some instances, the first slit 152a and the second slit 152b (shown in phantom line) may be arranged orthogonally and originate from opposite sides of the seal body 148, as depicted in FIG. 7. The first slit 152a, the second slit 152b or both may be cuts, perforations, or the like. Other arrangements are contemplated.

Figure 9:
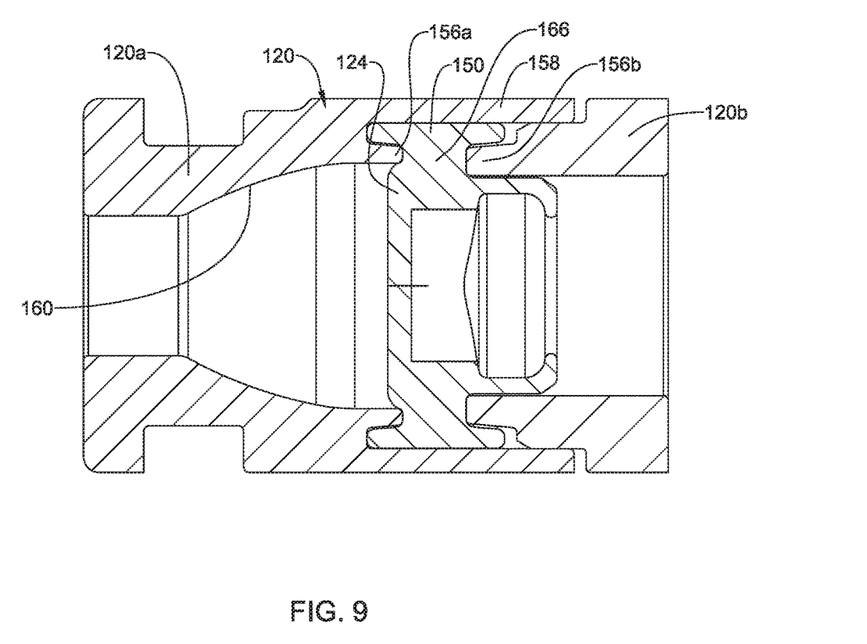
FIG. 9 is a cross-sectional view an example cartridge and an example seal member.

FIG. 9 illustrates an example cartridge 120. In this example, the cartridge 120 may include a first section 120a and a second section 120b. The seal member 124 may be coupled to the cartridge 120. This may include disposing the peripheral region 150 along a seal holding region of the cartridge 120 that may be defined by a pair of flanged regions 156a/156b and a top or outer region 158. In at least some instances, the seal member 124 may be mechanically secured to the cartridge 120 at the seal holding region. Mechanically securing the seal member 124 to the cartridge 120 may help hold the seal member 124 more securely so that the seal member 124 is less likely to shift or move when exposed to elevated pressures. Because of this, the seal member 124 is able to withstand higher pressures (e.g., on the order of about 80-400 psi, or more). In some instances, the peripheral region 150 of the seal member 124 may be crimped to the cartridge 120. This may include crimping the peripheral region 150 between the flanged regions 156a/156b, crimping the peripheral region 150 between the flanged region 156a and the outer region 158, crimping the peripheral region 150 between the flanged region 156b and the outer region 158, crimping the flanged region 156a to the shoulder region 166, crimping the flanged region 156b to the shoulder region 166, or combinations thereof. Other mechanical bonds are contemplated including mechanical press fitting, ultrasonic welding, adhesive bonding, or the like.

The first section 120a of the cartridge 120 may have enlarged internal section 160. In at least some instances, the enlarged internal section 160 has a rounded or partially spherical shape. The rounded shape of the enlarged internal section 160 may provide additional space for the seal member 124 to open up into when a device is passed there through. Thus, the enlarged internal section 160 may allow the seal member 124 to accommodate larger devices without become deformed or damaged.

The materials that can be used for the various components of the hemostasis valve 10 (and/or other hemostasis valves disclosed herein) and the various components thereof disclosed herein may include those commonly associated with medical devices. For simplicity purposes, the following discussion makes reference to the main body 12 and other components of the hemostasis valve 10. However, this is not intended to limit the devices and methods described herein, as the discussion may be applied to other hemostasis valves and/or components thereof disclosed herein.

The main body 12 and/or other components of the hemostasis valve 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:
1. A hemostasis valve, comprising:
a main body having a proximal end region;
a cartridge at least partially disposed within the proximal end region, the cartridge including a first seal member;
wherein the cartridge has a proximal member, a distal member, and defines a seal holding region;
wherein the main body includes a second seal member disposed within the proximal end region, wherein the first seal member is spaced apart from the second seal member;

wherein when the hemostasis valve is in a relaxed, unactuated configuration, the first seal member is in a closed position and the second seal member is in an open position;
wherein the second seal member is manually actuatable between the open position and a closed position by movement of the cartridge, and remains in the open position until manually actuated to the closed position;
wherein the first seal member has an axial thickness of 0.04-0.2 inches; and
wherein the first seal member is secured within the seal holding region by a mechanical bond.

2. The hemostasis valve of claim 1, wherein the mechanical bond includes a crimp.

3. The hemostasis valve of claim 1, wherein the first seal member has an axial thickness of 0.075-0.095 inches.

4. The hemostasis valve of claim 1, wherein the first seal member has a distal face with a distal slit, wherein the first seal member has a proximal face with a proximal slit; and wherein the distal slit and the proximal slit are axially spaced 0.01-0.02 inches.

5. The hemostasis valve of claim 4, wherein the distal slit is arranged orthogonally with the proximal slit.

6. The hemostasis valve of claim 1, further comprising a plunger coupled to the proximal end region of the main body, the plunger configured to slide distally to move the first seal member from the closed position to an open position, the plunger configured to be rotated to move the cartridge which moves the second seal member from the open position to the closed position.

7. The hemostasis valve of claim 1, wherein the first seal member has a seal body and a peripheral region designed to engage the seal holding region of the cartridge.

8. The hemostasis valve of claim 7, wherein the peripheral region has a radial thickness of 0.001-0.02 inches.

9. The hemostasis valve of claim 7, wherein the central seal region has a width that is at least twice as large as a radial thickness of the peripheral region.

10. The hemostasis valve of claim 1, wherein the proximal end region of the main body includes one or more threads and further comprising a nut threadably engaged with the one or more threads.

11. A hemostasis valve, comprising:
a main body having a threaded proximal end region;
a nut threadably engaged with the threaded proximal end region;
a plunger coupled to the threaded proximal end region;
a cartridge at least partially disposed within the threaded proximal end region, the cartridge including a first seal member;
wherein the main body includes a second seal member disposed within the threaded proximal end region, wherein the first seal member is spaced apart from the second seal member;
wherein the plunger is configured to move the first seal member from a closed position to an open position;
wherein the second seal member is manually actuatable by rotating the plunger to move the second seal member between an open position and a closed position, wherein the second seal member remains in the open position until manually actuated to the closed position;
wherein the first seal member is secured within a seal holding region of the cartridge by a mechanical bond; and
wherein the first seal member has an axial thickness of 0.04-0.2 inches.

12. The hemostasis valve of claim 11, wherein the mechanical bond includes a crimp.

13. The hemostasis valve of claim 11, wherein the first seal member has an axial thickness of 0.075-0.095 inches.

14. The hemostasis valve of claim 11, wherein the first seal member has a distal face with a distal slit, wherein the first seal member has a proximal face with a proximal slit; and wherein the distal slit and the proximal slit are axially spaced 0.01-0.02 inches.

15. The hemostasis valve of claim 14, wherein the distal slit is arranged orthogonally with the proximal slit.

16. The hemostasis valve of claim 11, wherein the first seal member has a central seal region and a peripheral leg region designed to engage the seal holding region of the cartridge.

17. The hemostasis valve of claim 16, wherein the peripheral leg region has a radial thickness of 0.001-0.02 inches.

18. The hemostasis valve of claim 16, wherein the central seal region has a width that is at least twice as large as a radial thickness of the peripheral leg region.

19. A hemostasis valve, comprising:
a main body having a threaded proximal end region;
a nut threadably engaged with the threaded proximal end region;
a plunger coupled to the threaded proximal end region;
a cartridge at least partially disposed within the threaded proximal end region, the cartridge including a first seal member;
wherein the first seal member is secured within a seal holding region of the cartridge by a crimp bond;
wherein the main body includes a second seal member disposed within the threaded proximal end region, wherein the first seal member is spaced apart from the second seal member;
wherein the plunger is configured to move the first seal member from a closed position to an open position;
wherein the second seal member is manually actuatable by rotating the plunger to move the second seal member between an open position and a closed position, wherein the second seal member remains in the open position until manually actuated to the closed position;
wherein the first seal member has a central seal region and a peripheral leg region designed to engage the seal holding region of the cartridge; and
wherein the central seal region has a width that is at least twice as large as a radial thickness of the peripheral leg region.

20. The hemostasis valve of claim 19, wherein the first seal member has an axial thickness of 0.075-0.095 inches.

* * * * *